United States Patent [19]

Fallin

[11] Patent Number: 4,990,149

[45] Date of Patent: Feb. 5, 1991

[54] RELEASABLE ORTHOPEDIC BROACH HANDLE APPARATUS

[75] Inventor: Thomas W. Fallin, Memphis, Tenn.

[73] Assignee: Richards Medical Company, Memphis, Tenn.

[21] Appl. No.: 301,159

[22] Filed: Jan. 24, 1989

[51] Int. Cl.⁵ ............................................. A61B 17/16
[52] U.S. Cl. ......................................... 606/85; 66/79; 16/114 R
[58] Field of Search ............ 128/92 VJ, 303 R, 92 V; 16/114 R, 114 A, DIG. 40, DIG. 24; 292/175; 403/325, 328; 623/18, 20, 22, 23; 606/79, 85

[56] References Cited

U.S. PATENT DOCUMENTS

| | | | |
|---|---|---|---|
| 2,639,158 | 5/1953 | Procos | 403/325 X |
| 3,243,213 | 3/1966 | Proctor | 403/325 |
| 4,218,940 | 8/1980 | Main | 81/63 |
| 4,583,270 | 4/1986 | Kenna | 128/92 VJ |
| 4,587,964 | 5/1986 | Walker et al. | 128/92 VJ |
| 4,601,289 | 7/1986 | Chiarizzio et al. | 128/92 VJ |
| 4,614,457 | 9/1986 | Sammon | 403/328 X |
| 4,739,750 | 4/1988 | Masse et al. | 128/92 VJ |
| 4,765,328 | 8/1988 | Keller et al. | 128/303 R |

Primary Examiner—Robert A. Hafer
Assistant Examiner—Kevin G. Rooney
Attorney, Agent, or Firm—Pravel, Gambrell, Hewitt, Kimball & Krieger

[57] ABSTRACT

A modular broach handle for use with a broach having a tapered configuration beginning at a wider upper end tapering to a smaller lower end. An elongated handle body portion has a longitudinal axis, with one end portion of the handle body defining a connection end portion for attaching a broach thereto at the wide upper end portion of the broach. A slot extends a distance along the handle terminating at one end thereof adjacent a connection end poriton of the handle body. A socket communicating with the slot is formed at the connection end portion of the handle body, the socket having an open end portion receptive of an attachment post on the wide end portion of the broach. A spring loaded slider bar is disposed within the slot for sliding movement therein and with respect to the handle between engaged and disengaged positions, and includes an end portion that extends into the socket when in the engaged position to form a connection with the post. The slider bar and handle socket form a releasable locking mechanism between the post of the broach and the handle that is perfected upon assembly by pushing the post into the socket, without manipulation of the slider bar.

15 Claims, 4 Drawing Sheets

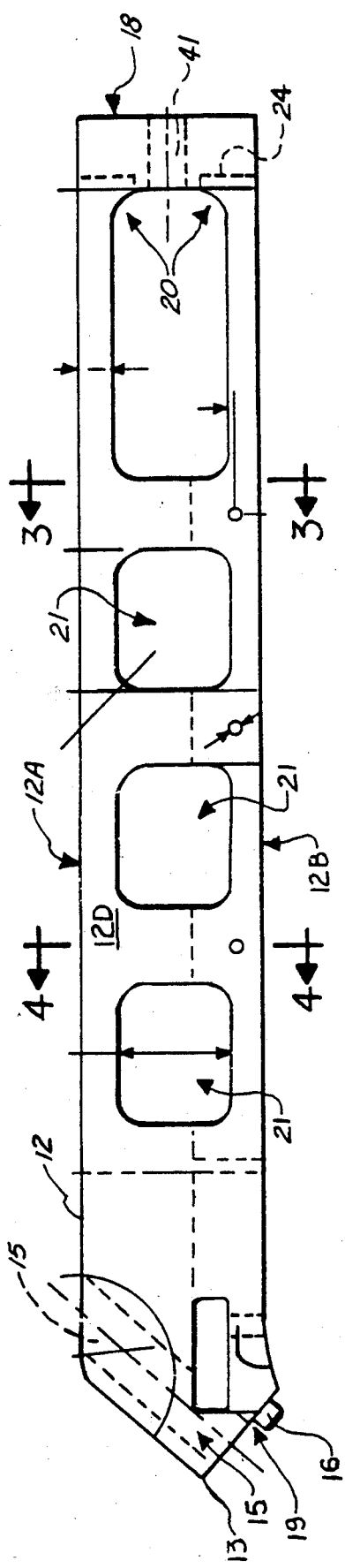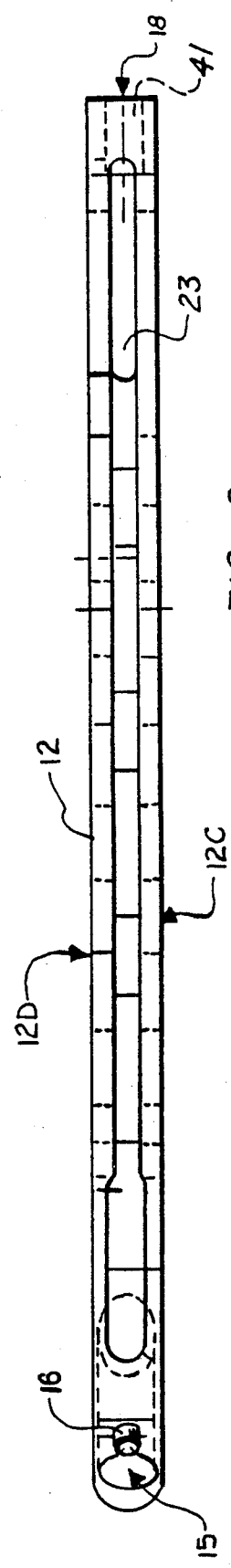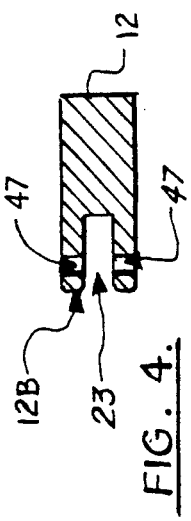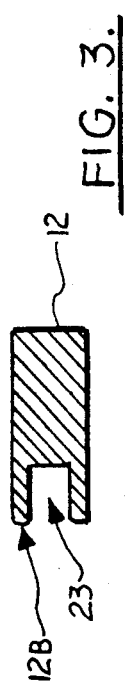

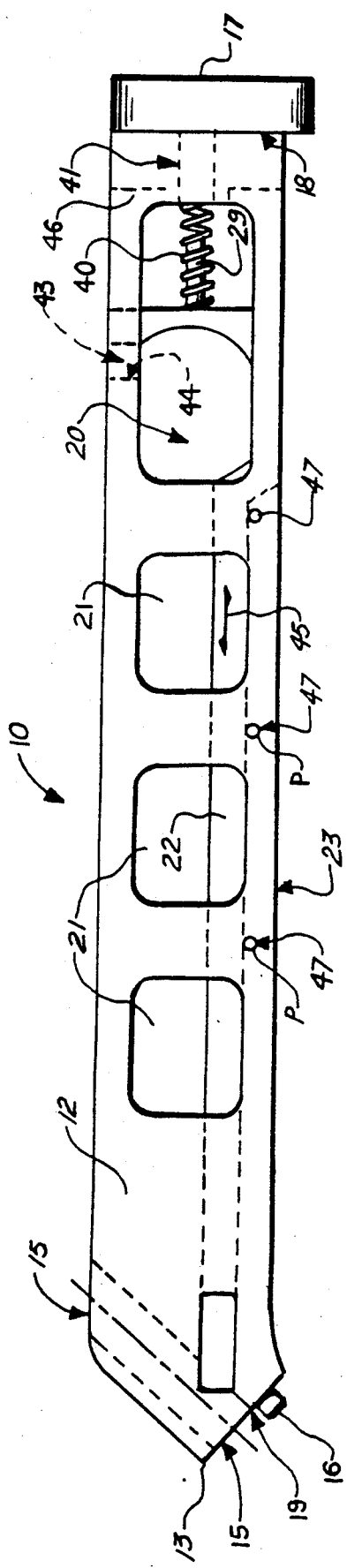
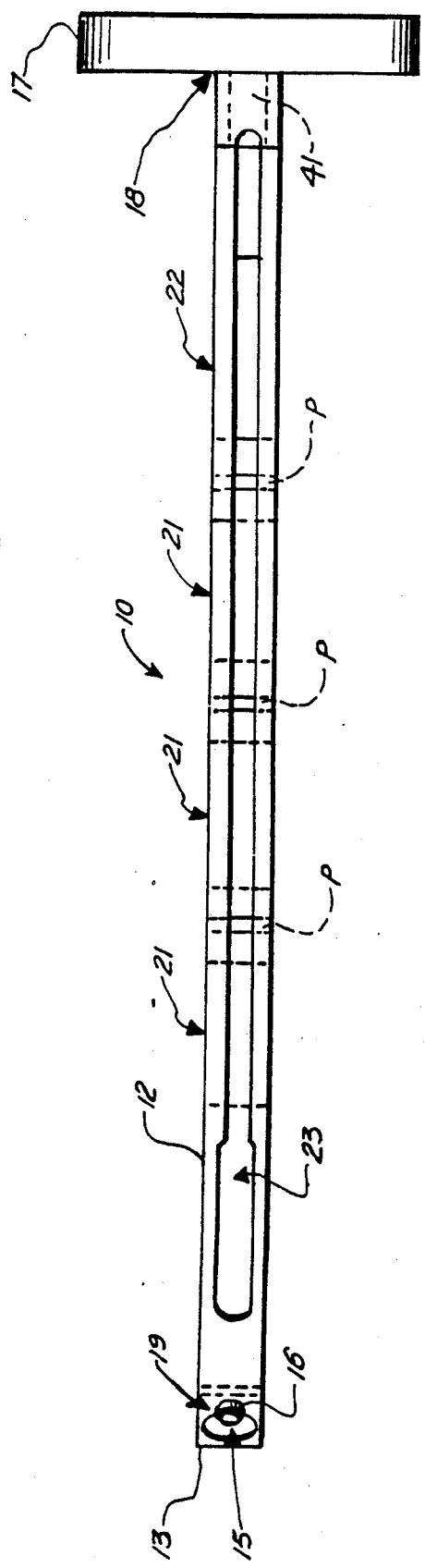
FIG. 7.
FIG. 8.

RELEASABLE ORTHOPEDIC BROACH HANDLE APPARATUS

BACKGROUND OF THE INVENTION

1. Field of the Invention

The present invention relates to modular broach and handle assemblies for use in orthopedic implant surgery. More particularly, the present invention relates to a modular broach handle construction featuring a locking mechanism for the broach that can be operated by surgeon without any special manipulative steps. The locking mechanism includes a trigger that moves a slider bar out of engagement with the broach so the handle can easily be disconnected and a spring that allows the handle to be locked onto the broach by simply pushing the components together.

2. General Background

Releasable broach or rasp handles have been used for the purpose of supporting a rasp in preparing a bone for receiving an implant. The handle is preferably releasable from the rasp following such use so other instruments can be used in preparing the bone while the portion inside the bone remains in place during other steps.

Typically, the broach or rasp is used during hip arthroplasty. The surgeon uses the broach to prepare the inner surfaces of the intermedullary canal to receive the stem of a femoral hip prosthesis. Surgical preparation of the intermedullary canal determines in large part the fit between the stem and femur and the accuracy of alignment.

The upper end of the broach is typically designed so other instruments can fit on it to prepare the upper surface of the femur. By using the broach as the reference point, accurate orientation of the prosthesis relative to the prepared bone is easier to achieve. A surgeon can also attach a trial neck and head to the upper end of the broach for performing a reduction in order to check range of motion, muscle tension, and leg length. Since hip surgery is a potentially dangerous and serious procedure, these instruments must be designed to provide a dependable connection that is easy to disengage.

Releasable broach or rasp and handle constructions have been developed in the past. Examples are shown in U.S Pat. No. 4,306,550, issued to Forte entitled "Combination Including Femoral Rasp And Calcar Facing Reamer"; U.S. Pat. No. 4,583,270, issued to Kenna, entitled "Rasp Handle"; and U.S. Pat. No. 4,601,289, issued to Chiarizzio et al., entitled "Femoral Trail Prosthesis/Rasp Assembly".

The Forte '550 patent provides a construction which includes a rasp having a cutting portion and a pilot post portion. A handle assembly with a chuck releasably engages the pilot post portion to facilitate working the rasp into a femur. A cutter device is adapted to be journaled on the pilot post and power driven to prepare the surface of the calcar adjacent the socket. After a socket is formed in the femur by use of a rasp and handle assembly, the rasp is left in the socket, the handle assembly is removed, and the cutter is journaled over the pilot post and rotated by a drive apparatus. However, the handle includes an enlongated transverse portion which extends away from the longitudinal axis of the handle. A transverse portion of this style, while workable, requires two hands to operate and extra manipulation to move the portion away from the handle.

The Kenna '270 patent includes a similar laterally extending portion of the handle. In the Chiarizzio et al. patent, a locking portion must pivot to a lateral position in order to disengage the broach from the handle, possibly interfering with other surgical instruments. These above-discussed patented devices require a preliminary manipulation of the locking mechanism in order to affix the broach to the handle.

SUMMARY OF THE PRESENT INVENTION

The present invention provides a modular broach handle apparatus which allows release of the handle from the broach simply by the physician pulling a trigger release located near the grip. Attachment and release is accomplished by a long rigid "slider" bar translating in a longitudinal slot of the handle in a superior-inferior direction against a compression spring.

The bar has a portion near the gripping end of the handle which can be pulled by the physician to overcome the force of the spring and disengage the handle from the broach. Engagement is achieved simply by pushing the handle in place, the pushing force overcoming the spring and moving the slider bar and allowing the handle to move into place with the slider bar moving back into its engagement position to lock the handle in place.

No part of the broach handle assembly extends beyond the rectangular outer "envelope" of the broach handle assembly. This permits use of a fork hammer for extraction while the handle is still in place. The direction of attachment and release is parallel to a cylindrical attachment post located on the superior face of the broach. Manual actuation of the slider bar is not necessary to connect the handle to the broach, as pushing the two parts together automatically actuates the locking mechanism.

The present invention thus provides an improved broach handle apparatus for use with a broach having a tapered configuration beginning at a wider upper end and tapering to a smaller lower end. The apparatus includes an elongated handle body portion having a longitudinal axis and one end portion defining a connection end portion for attaching the broach wide upper end thereto. A longitudinally extending slot extends a distance along the handle and terminates at one end thereof adjacent the connection end portion of the handle body.

A socket communicating with the slot and formed at the connection end portion of the handle body is provided, the socket having an open end portion receptive of at least a part of the wide end portion of the broach. A slider bar is disposed within the longitudinal slot for sliding movement therein and with respect to the handle between engaged and disengaged positions. The slider bar includes an end portion that extends into the socket when in the engaged position. An end portion of the slider bar and the handle socket form a releasable connection between the broach and the handle at a cylindrical connection post located on the superior face of the broach. A trigger is provided at one end of the slider bar for moving the slider bar within the longitudinal slot.

In the preferred embodiment, the handle has an outer surface defining an "envelope" and the longitudinal slot and slider bar are contained entirely within this envelope. The slider bar is spring loaded so that manual actuation of the slider bar is not necessary to connect the handle to the broach, as pushing the two parts (broach and handle) together automatically actuates the locking mechanism. The slider bar includes a trigger end portion which extends transversely with respect to the longitudinal axis of the handle, and at least one transverse opening is provided in the handle body which communicates with the trigger portion of the slider bar, for access purposes. The socket is cylindrical having a central bore corresponding to the broach cylindrical attachment post, with a bore axis that intersects the longitudinal axis of the handle at an acute angle.

BRIEF DESCRIPTION OF THE DRAWINGS

For a further understanding of the nature, objects, and advantages of the present invention, reference should be had to the following detailed description, taken in conjunction with the accompanying drawings, in which like reference numerals denote like elements, and wherein:

FIG. 1 is a side view of the broach handle body portion of the preferred embodiment of the apparatus of the present invention;

FIG. 2 is a bottom view of the broach handle body portion of the preferred embodiment of the apparatus of the present invention;

FIG. 3 is a sectional view taken along lines 3—3 of FIG. 1;

FIG. 4 is a sectional view taken along lines 4—4 of FIG. 1;

FIG. 7 is a side view of the preferred embodiment of the apparatus of the present invention;

FIG. 8 is a bottom view of the preferred embodiment of the apparatus of the present invention;

Figure 5:
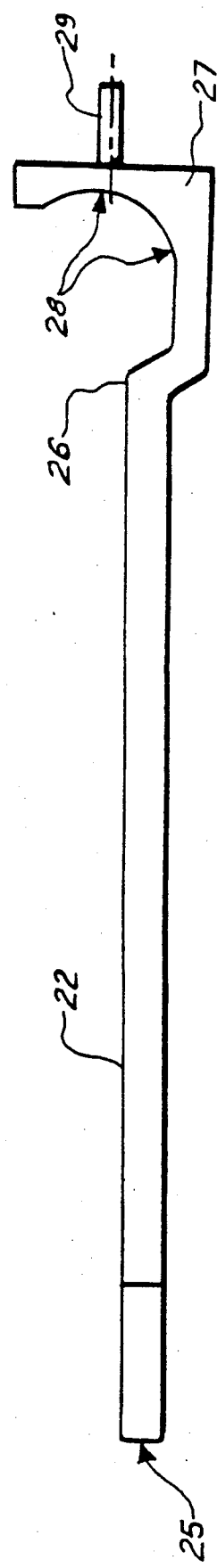
FIG. 5 is a fragmentary view of the preferred embodiment of the apparatus of the present invention illustrating the slider bar portion thereof.
Figure 6:
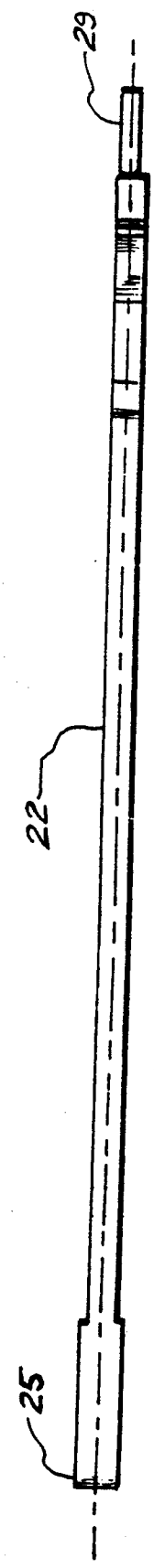
FIG. 6 is a top view of the slider bar portion of the preferred embodiment of the apparatus of the present invention.
Figure 10:
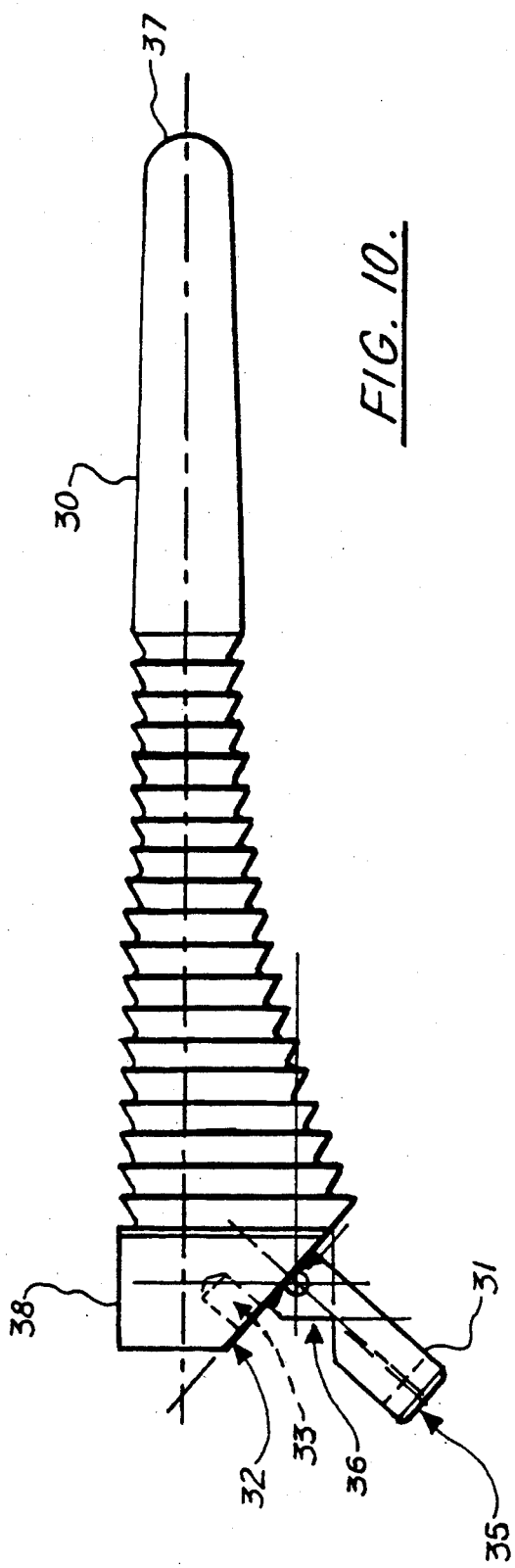
FIG. 10 is a side view of the broach portion of the preferred embodiment of the apparatus of the present invention.
Figure 9:
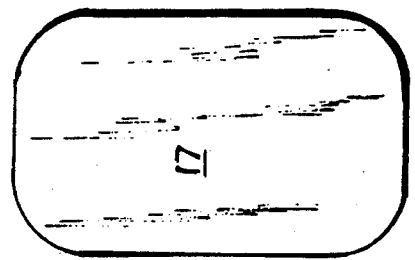
FIG. 9 is an end view of the handle body illustrating the driving platform portion thereof.
Figure 11:
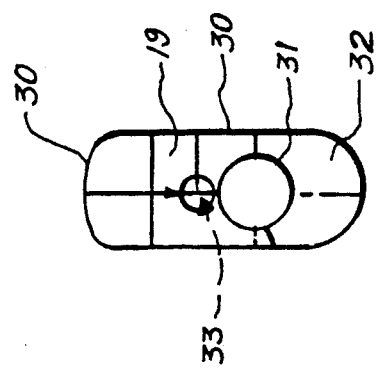
FIG. 11 is a top view of the broach portion of the preferred embodiment of the apparatus of the present invention taken along lines 11—11 of FIG. 10.

DETAILED DESCRIPTION OF THE PREFERRED EMBODIMENT:

FIGS. 1-11 illustrate the preferred embodiment of apparatus of the present invention which is designated in FIGS. 7 and 8 generally by the numeral 10. Modular broach handle apparatus 10 includes an elongated handle body 12 having an attachment 13 end portion for attaching broach 30 thereto, a rear end portion 18 and sidewalls 12A-12D. Broach 30 (FIGS. 10-11) provides a tapered body having wide upper end 38 tapering to smaller end 37. Wide end portion 38 has an attachment post 31 which is generally cylindrical and is adapted to register with and fit snugly within cylindrical bore 15 carried at the attachment 13 end portion of handle body 12.

The attachment 13 end portion of handle body 12 includes a generally flat face portion 19 which abuts a similar flat face portion 32 of broach 30. An alignment stud 16 extends away from surface 19 and is sized to register and fit within the alignment hole 33 of broach 30. The end portion 17 spaced away from attachment end 13 of handle body 12 defines a driving platform 17 which can be generally rectangular (see FIG. 9), and which affixes to handle body 12 at its rearmost face 18.

Handle body 12 provides a transverse opening 20 extending longitudinally (see FIG. 7) a distance to accommodate the finger of a surgeon for moving slider bar 22 fore and aft with respect to handle body 12. A plurality of additional openings 21 can be provided extending transversely through handle body 12 for reducing the weight of handle body 12.

Handle body 12 has a longitudinally extending slot 23 which extends substantially the length of handle body 12 terminating at rearmost stop 24 and extending forwardly to meet cylindrical bore 15.

In the preferred embodiment, the longitudinally extending slot 23 opens to the bottom surface 12B of handle body 12 for facilitating assembly of slider bar 22 into handle body 12 and more particularly into the longitudinally extending slot 23 portion thereof. Slider bar 22 (FIGS. 5-6) includes an elongated linear portion, generally rectangular in section, beginning at end 25 and terminating at 26. A trigger 27 includes a gripping surface portion 28 which is receptive of the finger of a surgeon. Trigger 28 includes spring carrier 29 which carries a coil spring 40 (FIG. 7) during operation. A spring socket 41 is provided in handle body 12 extending from the transverse opening 20 rearwardly to rear end portion 18 of handle body 12.

Handle body 12 includes an upper longitudinally extending slot 43 which defines a stop 44 limiting the forward movement of slider member 22 and a stop 46 limiting the rearward movement of slider member 22. The slider bar is free to translate longitudinally in a sliding fashion with respect to the handle body 12 in both directions as shown by the bi-directional arrow 45 in FIG. 7.

A plurality of openings 47 define pin openings for receiving assembly pins P, generally cylindrical in shape which are placed within openings 47 after slider bar 22 is placed in an operative position, as shown in FIG. 7. The assembly pins P can simply be force fit into position or held in place by means of cement, welding or the like.

The present invention provides a releasable connection which automatically connects broach 30 to handle body 12 when post 31 is placed into bore 15 in a direction which secures alignment pin 16 into opening 33 of broach 30 and which places the assembly faces 19 and 32 together in a face-to-face mating relationship.

Because the slider bar 22 moves longitudinally within slot 23, the end 25 portion of slider bar 22 is pushed rearwardly moving trigger 27 toward handle body end portion 18. However, when the outermost end 35 of assembly post 31 penetrates fully into bore 15, end 25 of slider bar 22 registers with recess 36 which is similarly shaped to end portion 25 so that a connection is formed between handle body 12 and broach 30 without the need for manipulation by the surgeon of the slider bar 22 and its trigger 27. Thus, the locking mechanism formed by end 25 of slider bar 22 registering with recess 36 of post 31 is automatic simply by forcing the broach and the handle body together, pushing the two parts 12, 30 together while registering post 31 into bore 15 and stud 16 into opening 33.

Upon assembly, the surgeon can then use the handle body 12 to manipulate the lowermost, narrow end portion 37 of broach 30 into the intermedullary canal as part of the surgical procedure. The opposite 38 wide end portion of broach 30 is connected to the handle until the surgeon pulls trigger 27 in a rearward direction, toward driving platform 17 which compresses coil spring 40.

The apparatus of the present invention can be manufactured of any suitable structural material, such as titanium, stainless steel, or the like, and/or any other metallic contruction which is useful for the manufacture of surgical instruments.

In view of the numerous modifications which could be made to the preferred embodiments disclosed herein without departing from the scope or spirit of the present invention, the details herein are to be interpreted as illustrative and not in a limiting sense.

What is claimed as invention is:

1. An improved broach handle for use with an orthopedic broach having a tapered configuration for preparing a bone to receive an implant, the broach including a tapered roughened portion and an upper end with a portion adapted to engage the handle, comprising:
   (a) an elongated handle body portion having a first portion defining a connection end adapted for connection to the upper end portion of the broach, and a second portion adapted to be gripped by a user;
   (b) socket means formed at the connection end portion of the handle body for receiving at least a portion of the end portion of the broach;
   (c) lock means in the form of a solid sliding member adapted for movement relative to the elongated handle body portion between engaged and disengaged positions, and including a first end portion adapted to extend into the socket and engage a cooperating portion of the upper end of the broach for locking the broach relative to the handle;
   (d) the lock means including a second end portion adapted to be disposed in the vicinity of the second portion of the handle body portion in an exposed position so that the lock means can be engaged and moved by the user with one hand when simultaneously gripping the handle body portion; and
   (e) spring means for urging the lock means toward the engaged position, the lock means being movable toward the disengaged position by the user.

2. The apparatus of claim 1, wherein the lock means includes a slider bar.

3. The apparatus of claim 1, wherein the handle includes an outer surface defining a envelope and a longitudinal slot contained entirely within the envelope for receiving the slider bar.

4. The apparatus of claim 3, wherein the second end portion of the lock means includes a trigger to be engaged by the user.

5. The apparatus of claim 4, further comprising at least one transverse opening in the handle body that communicates with the trigger, providing access for gripping of the trigger.

6. The apparatus of claim 1, wherein the socket means includes a central bore with an axis that intersects the longitudinal axis of the handle at an acute angle.

7. The apparatus of claim 1, further comprising alignment pin means projecting from the first end portion of the handle body portion for engaging a complimentary portion of the broach.

8. The apparatus of claim 3, wherein the slot communicates with an outer surface of the handle substantially along its length.

9. A modular broach handle apparatus comprising
   (a) a broach having a tapered configuration for preparing bone to receive an implant, the broach including at its outer end portion an attachment post projecting outwardly from the outer end portion;
   (b) an elongated handle having a first portion adapted for a connection to the outer end of the broach and a second portion adapted to be gripped by the user;
   (c) socket means at the first portion of the handle sized and shaped to receive the attachment post;
   (d) lock means in the form of a slid sliding member adapted for movement relative to the handle between engaged and disengaged positions and including an end portion adapted to project into the socket in the engaged position for engaging a cooperating portion of the post for locking the broach relative to the handle within the socket;
   (e) the lock means including a second end portion adapted to be disposed in the vicinity of the second portion of the handle body portion in an exposed position so that the lock means can be engaged and moved by the user when simultaneously ripping the handle body portion; and
   (f) spring means for urging the lock means toward the engaged position, the lock means being movable toward the disengaged position by the user.

10. The apparatus of claim 9, wherein the broach and handle have longitudinal axes which are generally parallel with respect to one another upon assembly of the broach and handle.

11. The apparatus of claim 9, wherein the broach includes a longitudinal axis and the attachment post has a central axis which forms an acute angle with the longitudinal axis of the broach.

12. The apparatus of claim 11, wherein the socket of the handle has a central bore axis which intersects the longitudinal axis of the handle at an acute angle.

13. The apparatus of claim 9, wherein the attachment post includes a recessed portion correspondingly shaped to register with one end portion of the sliding member so that when the sliding member is in the engaged position, an end portion of the sliding member nests and registers with the recess.

14. The apparatus of claim 9, wherein the lock means includes spring means for urging the sliding member to the engaged position.

15. The apparatus of claim 14, wherein the spring means includes a helical spring positioned between the sliding member and the handle.

* * * * *